(12) United States Patent
Tanaka et al.

(10) Patent No.: US 10,254,825 B2
(45) Date of Patent: Apr. 9, 2019

(54) BODY POSITION OPTIMIZATION AND BIO-SIGNAL FEEDBACK FOR SMART WEARABLE DEVICES

(71) Applicants: SONY CORPORATION, Tokyo (JP); SONY CORPORATION OF AMERICA, New York, NY (US)

(72) Inventors: Nobuo Tanaka, Glen Rock, NJ (US); Vladimir Elgort, Staten Island, NY (US); Jacelyn Danielson, San Mateo, CA (US); Anton Kalachev, Burlingame, CA (US); John Wong, Morristown, NJ (US); Behram DaCosta, San Jose, CA (US); Udupi Ramanath Bhat, Mountain View, CA (US); Ludovic Copere, San Jose, CA (US); Masaki Kataoka, Port Washington, NY (US)

(73) Assignee: SONY CORPORATION, Tokyo (JP)

( * ) Notice: Subject to any disclaimer, the term of this patent is extended or adjusted under 35 U.S.C. 154(b) by 166 days.

(21) Appl. No.: 15/236,465

(22) Filed: Aug. 14, 2016

(65) Prior Publication Data
US 2017/0010670 A1 Jan. 12, 2017

Related U.S. Application Data

(63) Continuation of application No. PCT/US2015/016679, filed on Feb. 19, 2015.
(Continued)

(51) Int. Cl.
*G06F 3/01* (2006.01)
*G06F 1/16* (2006.01)
(Continued)

(52) U.S. Cl.
CPC .............. *G06F 3/011* (2013.01); *G06F 1/163* (2013.01); *G06F 1/1637* (2013.01);
(Continued)

(58) Field of Classification Search
CPC .... G06F 19/3418; G06F 1/1626; G06F 1/163; G06F 1/1637; G06F 1/1698;
(Continued)

(56) References Cited

U.S. PATENT DOCUMENTS 9,797,729 B1* 10/2017 Lee ...................... G01C 21/165
9,867,125 B2* 1/2018 Eremenko ......... H04W 52/0203
(Continued)

FOREIGN PATENT DOCUMENTS

| JP | 2011-150408 A | 8/2011 |
|---|---|---|
| WO | 2010-082496 A1 | 7/2010 |

(Continued)

OTHER PUBLICATIONS

Japanese Patent Office (JPO), Official Action dated Dec. 4, 2017, related Japanese application No. 2016-551234, pp. 1-4, English-language translation, pp. 5-8, with claims examined, pp. 9-15.
(Continued)

*Primary Examiner* — Tony O Davis
(74) *Attorney, Agent, or Firm* — O'Banion & Ritchey LLP; John P. O'Banion (57) ABSTRACT

Smart wearable devices and methods are disclosed for providing feedback for optimal placement of the wearable device. This includes systems and methods to lock or unlock a wearable device and/or notify external wearable/non-wearable devices depending on the states of the wearer by sending notification or providing feedback if mispositioned or repositioned on the wearer. A system and method are disclosed for providing a user indication of proper placement of a wearable device by providing feedback based on
(Continued)

acquired bio-signal quality. In one embodiment, bio-signal quality is acquired by comparing a computed signal to noise ratio to that of an expected signal.

20 Claims, 7 Drawing Sheets

Related U.S. Application Data (60) Provisional application No. 61/943,837, filed on Feb. 24, 2014.

(51) Int. Cl.
```
G06F 1/3206      (2019.01)
G06F 1/3234      (2019.01)
G06F 1/3287      (2019.01)
G06F 19/00       (2018.01)
H04L 29/06       (2006.01)
H04W 12/06       (2009.01)
G16H 40/63       (2018.01)
G16H 40/67       (2018.01)
G08B 7/00        (2006.01)
```

(52) U.S. Cl.
CPC .......... *G06F 1/1698* (2013.01); *G06F 1/325* (2013.01); *G06F 1/3206* (2013.01); *G06F 1/3287* (2013.01); *G06F 3/015* (2013.01); *G06F 3/016* (2013.01); *G06F 19/00* (2013.01); *G06F 19/3418* (2013.01); *G16H 40/63* (2018.01); *G16H 40/67* (2018.01); *H04L 63/0861* (2013.01); *H04L 63/0869* (2013.01); *H04W 12/06* (2013.01); *G06F 1/1626* (2013.01); *G08B 7/00* (2013.01); *Y02D 10/171* (2018.01)

(58) Field of Classification Search
CPC ...... G06F 1/3206; G06F 1/325; G06F 1/3287; G06F 3/011; G06F 3/015; G06F 3/016; G08B 7/00; G16H 40/63; H04L 63/0861; H04L 63/0869; H04W 12/06
USPC ........................................................ 345/156
See application file for complete search history.

(56) References Cited

U.S. PATENT DOCUMENTS

| | | | |
|---|---|---|---|
| 2001/0043514 A1* | 11/2001 | Kita | A44C 5/0015 368/281 |
| 2007/0265741 A1 | 11/2007 | Oi et al. | |
| 2007/0279852 A1* | 12/2007 | Daniel | A44C 5/0007 361/679.03 |
| 2010/0312297 A1 | 12/2010 | Volpe et al. | |
| 2011/0071416 A1 | 3/2011 | Terada et al. | |
| 2011/0214158 A1* | 9/2011 | Pasquero | G06F 21/35 726/2 |
| 2012/0071743 A1* | 3/2012 | Todorov | G06F 19/3481 600/372 |
| 2012/0249741 A1* | 10/2012 | Maciocci | G06F 3/011 348/46 |
| 2012/0259377 A1 | 10/2012 | Freeman | |
| 2012/0271121 A1* | 10/2012 | Della Torre | A61B 5/024 600/301 |
| 2014/0288435 A1* | 9/2014 | Richards | A61B 5/02427 600/479 |
| 2015/0032505 A1* | 1/2015 | Kusukame | G06Q 30/0201 705/7.31 |
| 2015/0145653 A1* | 5/2015 | Katingari | G06F 1/163 340/12.3 |
| 2015/0170504 A1* | 6/2015 | Jooste | A61B 5/6898 340/539.12 |
| 2015/0177811 A1* | 6/2015 | Bose | G06F 1/3287 713/324 |
| 2015/0177841 A1* | 6/2015 | VanBlon | G06F 3/017 715/863 |
| 2015/0182130 A1* | 7/2015 | Utter, II | A61B 5/0205 600/483 |
| 2015/0186609 A1* | 7/2015 | Utter, II | A61B 5/0022 600/301 |
| 2015/0220154 A1* | 8/2015 | Midholt | G06F 3/017 345/156 |
| 2015/0227180 A1* | 8/2015 | Rabii | G06F 1/26 713/323 |
| 2015/0235474 A1* | 8/2015 | Mullins | G06T 19/006 345/419 |
| 2015/0272457 A1* | 10/2015 | Etemad | A61B 5/02438 600/509 |
| 2015/0272483 A1* | 10/2015 | Etemad | A61B 5/0488 600/409 |
| 2015/0272501 A1* | 10/2015 | MacEachern | A61B 5/0531 600/301 |
| 2016/0049004 A1* | 2/2016 | Mullins | G06T 19/006 345/419 |
| 2016/0070439 A1* | 3/2016 | Bostick | G06F 3/04842 715/728 |
| 2016/0089524 A1* | 3/2016 | Anderson | G08C 17/02 604/20 |
| 2016/0178906 A1* | 6/2016 | Rider | G02B 27/0172 726/17 |
| 2016/0217612 A1* | 7/2016 | Petill | G06T 19/006 |
| 2016/0249174 A1* | 8/2016 | Patel | G01K 13/002 |
| 2016/0317060 A1* | 11/2016 | Connor | A61B 5/4866 |
| 2016/0378193 A1* | 12/2016 | Camacho Perez | G06F 3/017 345/156 |
| 2017/0083102 A1* | 3/2017 | Dow | G06F 3/017 |
| 2017/0185142 A1* | 6/2017 | Zhang | G06F 3/011 |
| 2017/0235341 A1* | 8/2017 | Huitema | G06F 1/1652 361/679.03 |
| 2017/0237899 A1* | 8/2017 | Wexler | H04N 5/23222 348/207.11 |
| 2018/0054897 A1* | 2/2018 | Huitema | H05K 5/0086 |

FOREIGN PATENT DOCUMENTS

| | | |
|---|---|---|
| WO | 2013/032710 A1 | 3/2013 |
| WO | 2012/170924 A2 | 12/2013 |

OTHER PUBLICATIONS

European Patent Office (EPO), extended European search report dated Sep. 29, 2017, related European application No. 15751666.7, pp. 1-8, with claims searched, pp. 9-11.

Japanese Patent Office (JPO), Official Action issued Aug. 14, 2017, related Japanese application No. 2016-551234, pp. 1-9, English-language translation, pp. 10-20, with claims examined,pp. 21-28.

United States Patent and Trademark Office (UPSTO), International Search Report and Written Opinion, PCT International Application No. PCT/US2015/016679, pp. 1-9, with claims searched, pp. 10-17.

Korean Intellectual Property Office (KIPO), Notice of Preliminary Rejection dated May 31, 2018, related Korean patent application No. 10-2016-7021759, pp. 1-11, English-language translation, pp. 12-22, claims examined, pp. 23-29.

\* cited by examiner

BODY POSITION OPTIMIZATION AND BIO-SIGNAL FEEDBACK FOR SMART WEARABLE DEVICES

CROSS-REFERENCE TO RELATED APPLICATIONS

This application is a 35 U.S.C. § 111(a) continuation of PCT international application number PCT/US2015/016679 filed on Feb. 19, 2015, incorporated herein by reference in its entirety, which claims priority to, and the benefit of, U.S. provisional patent application Ser. No. 61/943,837 filed on Feb. 24, 2014, incorporated herein by reference in its entirety. Priority is claimed to each of the foregoing applications.

The above-referenced PCT international application was published as PCT International Publication No. WO 2015/127119 A2 on Aug. 27, 2015, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to smart wearable devices.

2. Discussion

One type of wearable device measures parameters related to the body, for example pulse rate, or respiration rate, or EMG, or spatial range of limb motion, etc. Accuracy and/or efficiency of such measurements can be affected by placement of the wearable device on the body.

The optimal placement of a wearable device on the body is often not apparent to the user/wearer of the wearable device. This can be due to a number of reasons. For example, the user/wearer would normally not have sufficient knowledge of the signal being measured or the technology being used for measurement, and hence would not know the optimal placement to improve performance of the wearable device via improved signal measurement. From a usability perspective, the user should not be burdened with requirements of such knowledge. Further, even expert users skilled in physiology and biosensors may not be able to ascertain the best position of placement without detailed measurements, since the signals of interest generated or related to the body are not directly observable by the user/wearer. Using the example of an ECG sensing wearable device above, the user may not realize that the wearable device's performance specifications would prevent it from measuring an ECG signal when placed vertically on the person's chest, or in any orientation on a the person's lower arm.

For instance, a smart-watch may not be able to detect if it is worn on the left or right wrist, at which exact position on the arm, how tightly fitting (or loose) on the wrist. Similarly, a set of wearable smart-glasses does not generally have any precise measurement of the wearer's eye distance, nose shape, or position of the branches of the frame around the ears. This has an implication not only to get the most accurate reading for a wearer, but also to adapt the sensing parameters to each individual's morphology. Indeed, today's wearable devices are generally only relying on user-input parameters (e.g. age, gender, height, weight . . . ) to fine-tune their algorithms, but this may be very coarse and imprecise given the unique characteristics of body shapes, internal organs' positioning (and ethnical variations).

Having multiple physical sizes for wearable devices is a primitive solution, but increases the overall cost structure for vendors/OEMs (and distributors) as multiple models have to be carried through. This therefore results in sub-optimal sensing and also the inability for a wearable device to inform the wearer about the fact that it is currently not positioned correctly—or where the optimal position would be in the wearer's unique case.

BRIEF SUMMARY

Smart wearable devices and methods are disclosed having feedback for optimal placement of the wearable device. This includes systems and methods to lock or unlock a wearable device and/or notify external wearable/non-wearable devices depending on the states of the wearer by sending notification or providing feedback if mis-positioned or repositioned on the wearer.

One aspect of the present technology is a system and method for providing for the wearable device to become "self-aware" of its own positioning (such as absolute and relative location on the body, ankle, and tightness of fitting . . . ) and its dynamic evolution over time. This information can be stored and used by the wearable device itself, as well as uploaded in the background to remote/Cloud-based server systems for various decision-making or notification.

Another aspect is smart wearable devices and methods having bio-signal feedback for optimal placement of the wearable device.

A further aspect of the present technology is a system and method for providing a user indication of proper placement of a wearable device by providing feedback based on acquired bio-signal quality. In one embodiment, bio-signal quality is acquired by comparing a computed signal to noise ratio to that of an expected signal.

In one embodiment, a feedback signal is generated via the emission source, wherein the feedback signal indicates a proximity of the one or more sensors with respect to the biometric signal as a function of the one or more signal properties of a biometric signal. In the case here signals from more than one sensors are considered in the estimation of signal properties, these sensors may be on the same physical device, or may be distributed across more than one physical device. Typically, the more than one physical devices in this case sense signals from the same user.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

The present disclosure generally pertains to wearable devices that are capable of, for example, performing an action based on one or more biological or physiological characteristics of the user wearing the device. Using one or more sensors, a processor, and code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood coritzol level, blood pressure, cholesterol, lactic acid level, body fat, protein level, hormone level, muscle mass, pH, etc. Such conditions may also include, but are not limited to, position (e.g., prone, upright), movement, or physical state (e.g., sleeping, exercising), etc.

A wearable device may include one or more output devices that include, but are not limited to, haptic output devices (e.g., offset motors, electroactive polymers, capacitive voltage generators, Peltier temperature elements, contracting materials, Braille coding actuators), telemetry devices, visual devices, audible devices, and other output devices.

A wearable device may include artificial intelligence so that the device can learn and adapt to the wearer. The device may be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device may also include one or more cameras or other visual sensors for facial, user, or other image recognition. A wearable device may also be configured to transmit information to and/or retrieve information from a wearer's digital health history.

A wearable device may be configured to output information to a user, to another wearable device, to a non-wearable device, or to a network according to the particular features and function of the device.

A. Generalized System Implementation.

Figure 1:
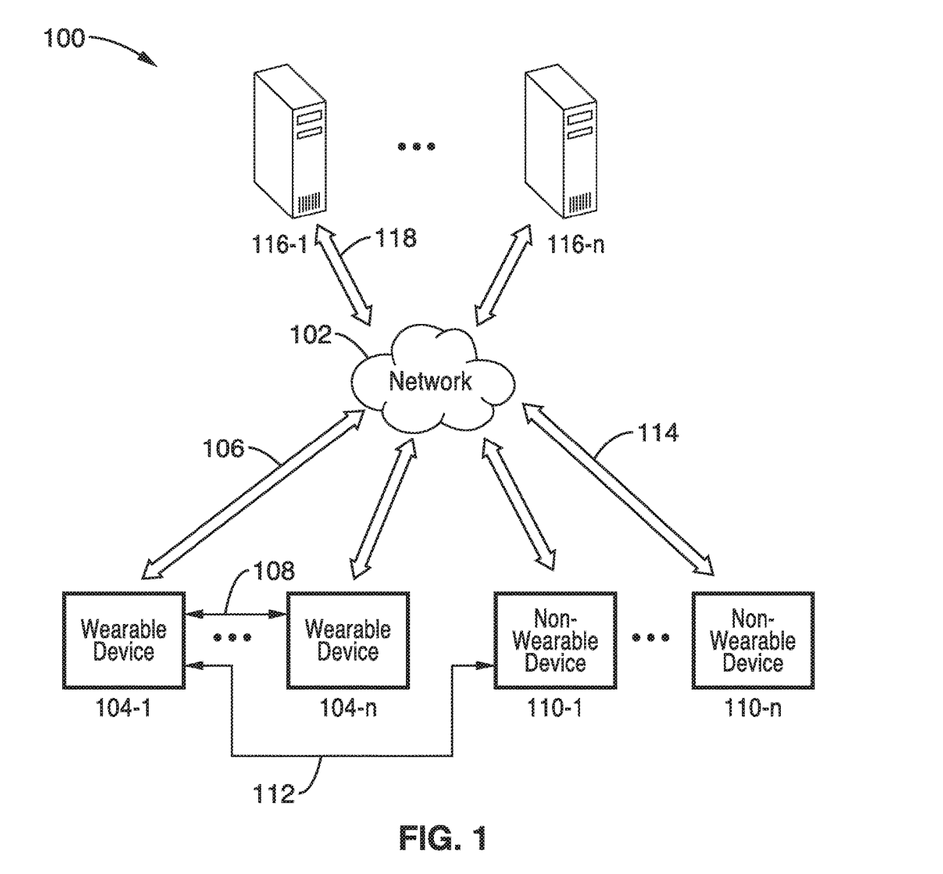
FIG. 1 is a schematic diagram of an embodiment of a smart wearable network described herein.

FIG. 1 illustrates a generalized networked infrastructure (e.g., system) 100 that includes a network 102. The network could, for example, be a local area network or a wide area network such as the Internet. One or more smart wearable devices 104-1 through 104-n according to embodiments of the technology described herein may be enabled to communicate with the network 102 through a wired or wireless connection 106. Further, one or more of the smart wearable devices may be enabled to communicate with another smart wearable device through the network 102 or by means of a direct wired or wireless connection 108.

One or more of the smart wearable devices 104-1 through 104-n also may be enabled to communicate with one or more non-wearable devices 110-1 through 110-n. The non-wearable devices, which are beyond the scope of this disclosure, may be any conventional "smart" device with a processor, associated operating system, and communications interface. Examples of non-wearable devices include Smartphones, tablet computers, laptop computers, desktop computers, and set top boxes. Any of the non-wearable devices may be of a type enabled to communicate with an external device through a wired or wireless connection. In that case, one or more of the smart wearable devices may be enabled to communicate with one or more of the non-wearable devices by means of a direct wired or wireless connection 112. Further, one or more of the non-wearable devices may be of a type enabled to communicate with the network 102 through a standard wired or wireless connection 114. In that case, one or more of the smart wearable devices may be enabled to communicate with one or more of the non-wearable devices through the network 102.

One or more servers 116-1 through 116-n may be provided in a client-server configuration and connected to the network by means of a wired or wireless connection 118. The servers may include standalone servers, cluster servers, networked servers, or servers connected in an array to function like a large computer. In that case, one or more of the smart wearable devices may be enabled to communicate with one or more of the servers.

Figure 2:
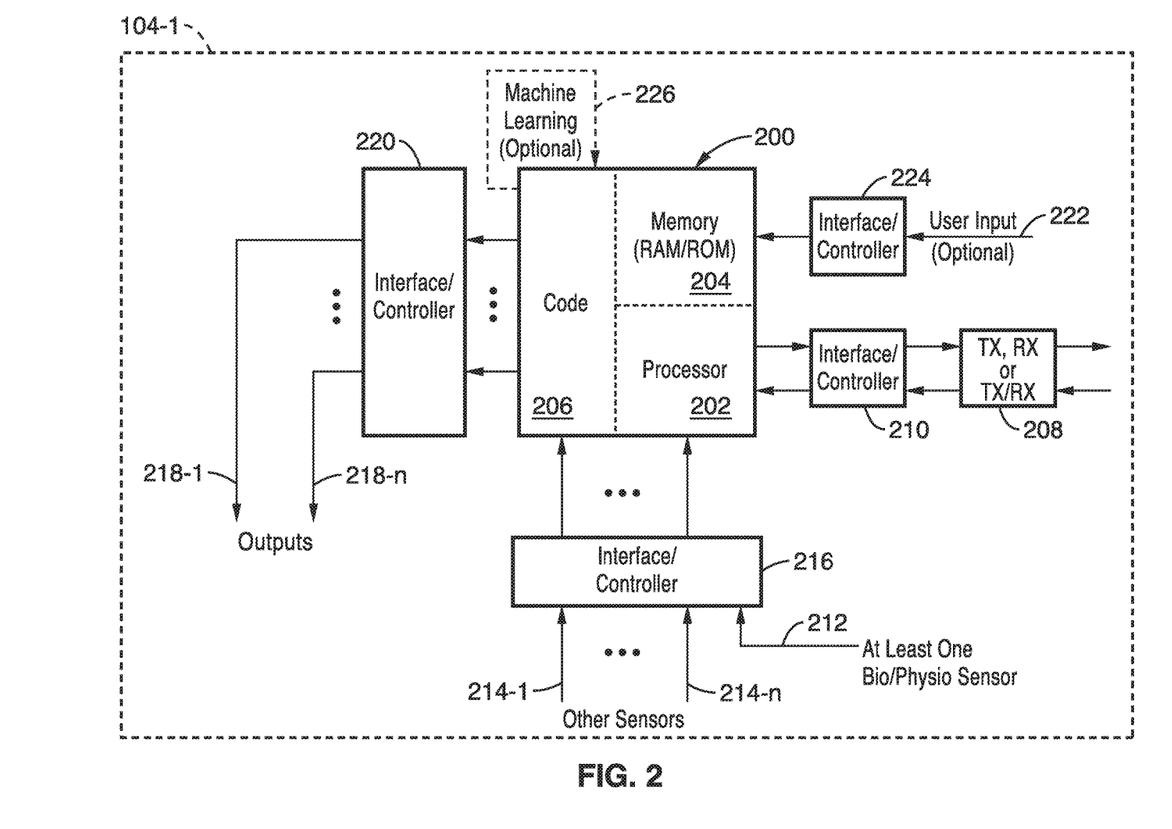
FIG. 2 is a functional block diagram of an embodiment of a smart wearable device described herein.

FIG. 2 illustrates a generalized embodiment of a smart wearable device according to the technology described herein. It will be appreciated that the embodiment shown may be modified or customized to enable performing the functions described herein. In the exemplary embodiment shown, the smart wearable device includes an "engine" 200 having a processor 202, memory 204, and application software code 206. The processor 202 can be any suitable conventional processor. The memory 204 may include any suitable conventional RAM type memory and/or ROM type memory with associated storage space for storing the application programming code 206.

A conventional wired or wireless communications module 208 (e.g., transmitter or receiver or transceiver) may be included as needed for performing one or more of the functions of the smart wearable device described herein. Examples of wireless communication capabilities that can be provided include, but are not limited to, Bluetooth, Wi-Fi, infrared, cellular, and near field communication. One or more conventional interfaces or controllers 210 may also be provided if needed. Examples of interfaces or controllers include, but are not limited to, analog to digital converters, digital to analog converters, buffers, etc.

The device may include at least one input 212 for a biological or physiological sensor for providing input to the device to perform one or more of the functions described herein. Sensor inputs 214-1 through 214-n for optional sensors may be included as well. These optional input sensors may include, but are not limited to, accelerometers, temperature sensors, altitude sensors, motion sensors, position sensors, and other sensors to perform the function(s) described herein. One or more conventional interfaces or controllers 216 may be provided if needed for the sensors. Examples of interfaces or controllers include, but are not limited to, analog to digital converters, digital to analog converters, buffers, etc.

Additionally, the device may include one or more outputs 218-1 through 218-n to drive one or more output devices (and include those output devices). These output devices may include, but are not limited to, haptic output devices, telemetry devices, visual devices, audible devices, and other output devices to perform the functions described herein. One or more conventional interfaces or controllers 220 may be provided if needed for the output devices. Examples of interfaces or controllers include, but are not limited to, analog to digital converters, digital to analog converters, buffers, etc.

A user input 222 may be provided according to the functions described herein. The user input may, for example, initiate one or more functions, terminate one or more functions, or intervene in a running process. The user input can be any conventional input device, including but not limited to, manual switches, touch sensors, magnetic sensors, proximity sensors, etc. One or more conventional interfaces or controllers 224 may be provided if needed for the output devices. Examples of interfaces or controllers include, but are not limited to, analog to digital converters, digital to analog converters, buffers, etc.

Depending on the function(s) described herein, the engine 200 may also include a feedback loop 226 for machine learning or other adaptive functions. The feedback loop may also provide for device calibration.

It will be appreciated that a smart wearable device as described herein would necessarily include a housing or carrier for the above-described components. It will further be appreciated that, as used herein, the term "smart wearable device" means a device that would be worn or otherwise associated with the body of a user and be "connected" to the user by means of at least one sensor for sensing one or more biological or physiological conditions of the user.

The particular form of the housing or carrier (i.e., wearable platform) can vary according to choice and suitability for performing the functions described herein. Examples of wearable platforms include, but are not limited to, hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, gloves, etc.

It will further be appreciated that the input sensors and output devices may be integrated into the wearable platform, or may be external to the wearable platform, as is desired and/or suitable for the function(s) of the smart wearable device.

B. Smart Wearable Device with Bio-Signal Feedback

The disclosed devices and methods facilitate the acquisition of accessible feedback regarding placement of the wearable device on the body. As used herein, the term "body" may comprise the wearer's own body, or another person's body, or body of another animal or living thing. As used herein, the term "accessible" refers to feedback that can be perceived by the user using regular senses such as sight, hearing, touch, etc.

Figure 3:
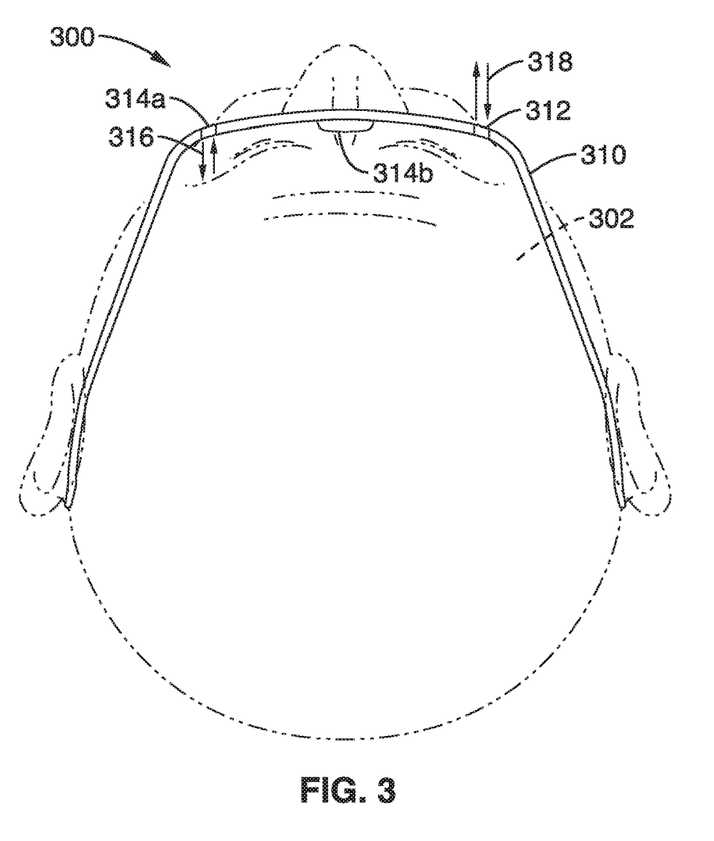
FIG. 3 is a schematic diagram of an embodiment of a smart wearable device in the form of eye-wear having positional feedback.

Presented in FIG. 3 is a schematic diagram of eyewear 300 (e.g. "smart glasses") for providing location feedback with respect to a wearable device, e.g. in accordance with smart wearable device 104-1 (see FIG. 1 and FIG. 2) and one or more signals. In addition to biological/physiological sensors, the wearable device 300 has one or more dedicated sensor(s) embedded, attached, or otherwise coupled to frame 310 for the sole purpose of acquiring position data to measure the position/state of the wearable device 300, and/or biological/physiological sensors, with respect to the user.

For example, the nose pads 314b of smart-glasses may include a pressure sensor to detect when the pair of glasses is being lifted from the wearer's face 302.

Sensor 314 a may be a combined-purpose sensor for detecting the position/state of the wearable device 300 with respect to the user 302, and also be used to detect biological/physiological signals of the user 302. For example, sensor 314a may send an illumination signal 316 toward the patients retina (e.g. retina scanner) for the purpose of acquiring biometric data with respect to the user 320, while also providing information about the location of the glasses 300 with respect to the user 302 (e.g. for calibration).

Sensor 312 may be purposed as a dedicated biometric/physiological sensor for measuring signal 318 that is wholly unrelated to calibration or the position/state of the device 300 with respect to the user 302.

Figure 4:
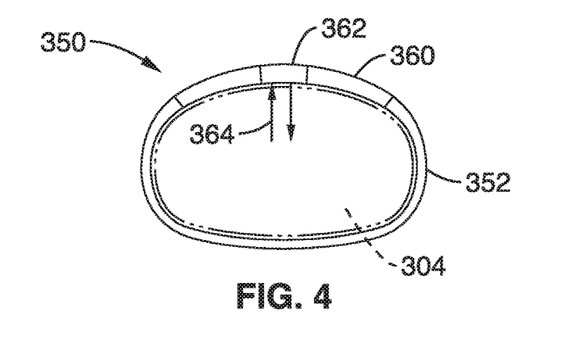
FIG. 4 is a schematic diagram of an embodiment of a smart wearable device in the form of a wrist strap having positional feedback.

FIG. 4 shows an exemplary wrist-based sensing wearable device 350 having a housing 360 and wrist band 352 that re-uses one or more existing sensors 362 (which are actively participating in the useful sensing of body parameters of user 304 via signal 364) for the purpose of the wearable device's own calibration of the position/state of the device 350. This may be achieved through a combination of measuring skin contact/conduction, acceleration and gyroscopy, or other sensing measurements. It is appreciated that wearable device 350 may also have dedicated components/sensors for calibration, as shown in wearable device 300.

The dual or sole purpose sensors shown in FIG. 3 and FIG. 4 may comprise one or more of tension/pressure-sensitive sensors embedded into fabric/textile, jitter sensor (to detect loose fitting), pressure/contact sensor on the watch's wristband (to know at which hole is the watch's hook attached) or on the nose pads of smart-glasses (to detect when the pair of glasses is being lifted from the wearer's face), among other types of sensors known in the art.

It is appreciated that the systems and methods of the present disclosure may be used on a number of devices for measuring different types of biometric signals where location of the sensors has an impact on the environmental/biological data being acquired. For example, system 350 may be configured for use in acquiring pulse rate for a heart rate monitor, EMG, spatial range of limb motion, blood oxygenation for a pulse oximeter, temperature, etc.

Figure 5:
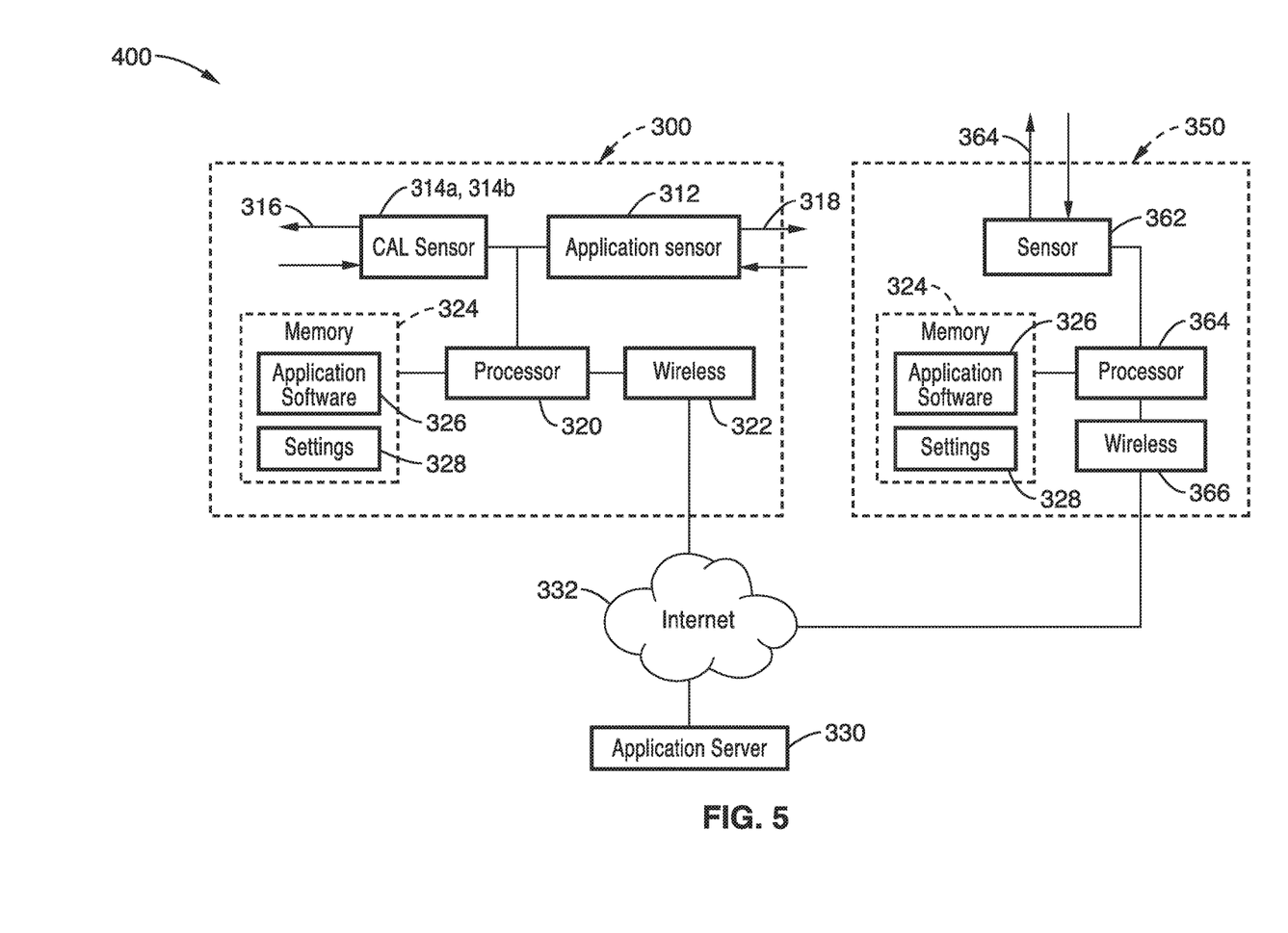
FIG. 5 is a schematic component diagram of embodiments of a system of smart wearable devices having positional feedback in accordance with the present description.

FIG. 5 shows a schematic diagram of a system 400 of components comprising the eyewear 300 and wrist band 350. It is appreciated that wearable devices 300 and 350 may also include additional circuitry as shown in the wearable device 104-1 in FIG. 2.

Sensors 312, 362 may receive signals 316, 364 respectively that are used for calibrating devices 300, 350. In the case of device 350, signal 364 may also be a biometric signal, whereas for device 300 only signal 316 is used for calibration via calibration sensor 314a or 314b, and biometric signal 318 and 318 is received by application sensor 318. Devices 300, 350 preferably both comprise memory for holding application software 326 that drives calibration processes on processor 320, as well as for storing calibration settings 328 of varying strength depending on the location of the sensors 312. Upon receiving the biometric signals, 318 (or 364 for device 350) the application programming 326 (which may comprise code 206 in FIG. 2, or a module thereof) may also analyze the incoming data for various purposes.

Wireless circuitry/interface 322, 366 (e.g. Wifi, Bluetooth, etc.) may also be provided so that data can be sent to or received from (in an encrypted way to ensure privacy and anonymity) to a remote/Cloud-based application server 330 (e.g. over Internet 332), whose access would be granted (or revoked) to 3rd-parties such as healthcare professionals, live venues, pharmaceutical companies so that they would set the specific rules governing the position and removal of the wearable device. Once those rules are set, they can be pushed automatically in a dedicated, secure (and temperproof) part (e.g. settings module 328) of the wearable device's internal memory 324, so that the wearable device's processing algorithms 326 get the reference of optimal position, as well as the set of action to trigger whenever the wearable device 300, 350 is removed from the wearer's body.

In one embodiment, feedback signal (not shown) may comprise an audible sound indicating placement on the human body, with the amplitude of the sound increasing as the signal strength (e.g. SNR or the like) increases.

Figure 6:
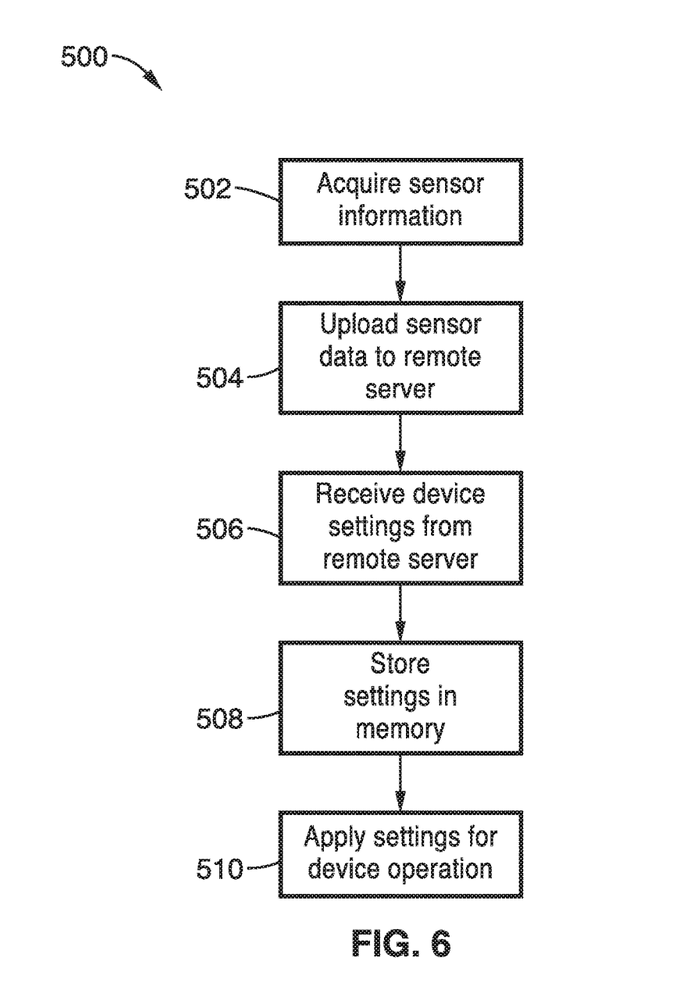
FIG. 6 shows a flow diagram of a method for providing positional feedback for a wearable device as described herein.

FIG. 6 illustrates a method 500 for providing positional feedback for a wearable device in accordance with the present description. Method 500 may be implemented as application programming 326 (FIG. 5) and/or code 206 (FIG. 2). At step 502, the sensor information (e.g. biosignals 316 or 364) are acquired by the sensors (e.g. 314a, 314b or 362). Pre-processing may be performed at this step (e.g. filtering, amplification, and then processed in analog domain or digitized and processed in digital domain, and in spatial and/frequency domain). Pattern recognition may also be applied to identify the signal of interest (in either digital or analog domain).

At step 504, the acquired data is uploaded to a remote server (e.g. application server 330). Pre-processing and pattern recognition may also be performed at the remote server 330.

At step 506, the device settings may be retrieved from the remote server 330, and then stored in memory 328 at step 508.

At step 510, the retrieved settings may then be applied to the device as a function of the acquired data from step 502 for adjustment of one or more parameters of the device for daily operation of the wearable device 300, 350, particularly in light of functionality in sensing biometric data from the user.

The position optimization systems and methods may be used in a wide variety of applications, such as, but not limited to:

1) Informing a patient of the most optimal positioning location for a health tracker based on his own physical condition or treatment. Such device may also include hardware and software for notifying healthcare professional in case such position remains sub-optimal for a certain period of time, or when the wearable device is removed altogether from the wearer's body while it supposed to be worn given a specific time period.

2) Implementation in wearable entertainment devices (such as wearable controls for video-gaming, e.g. bodily worn game controllers), thus negating the need for manual calibration by the user.

3) Ensuring compliance for healthcare monitoring, e.g. ensuring that the patient does keep their wearable device tracking their body signals at all the times configured by the healthcare professionals or pharmaceutical company.

4) Avoiding forgery or illicit usage (e.g. in this case, the wearable device 300, 350 also holds information in memory 324 that corresponds to an electronic ticket to amusement parks, venues or live events, and removal of the wearable device 300, 350 from wearer A to wearer B (as sensed by sensor 362, 312, etc., e.g. via body temperature or other biometric signal 318, 364) would automatically void the credit or transaction).

C. Smart Wearable Device with Bio-Signal Feedback

The disclosed devices and methods facilitate the acquisition of accessible feedback regarding placement of the wearable device on the body. As used herein, the term "body" may comprise the wearer's own body, or another person's body, or body of another animal or living thing. As used herein, the term "accessible" refers to feedback that can be perceived by the user using regular senses such as sight, hearing, touch, etc. The feedback may be provided to the wearer, or to a person other than the wearer of the device. In the latter case, the non-wearer may be attaching the device to the wearer.

Figure 7:
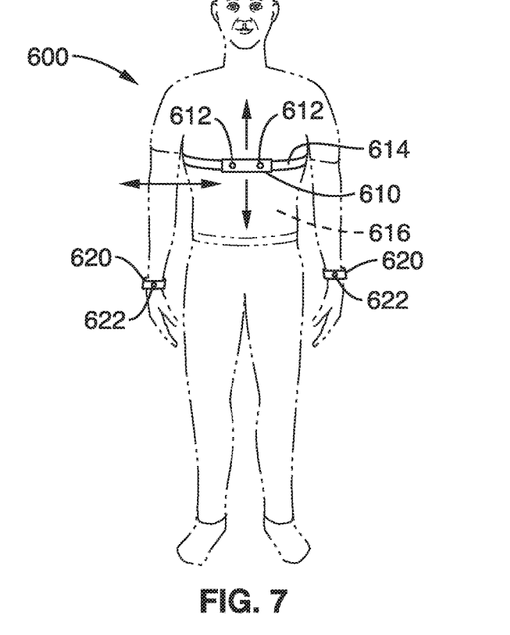
FIG. 7 is a schematic diagram of an embodiment of a smart wearable device and system having bio-signal feedback.

Presented in FIG. 7 is a schematic diagram of a system 600 for providing location feedback with respect to a wearable device, e.g. in accordance with smart wearable device 104-1 (see FIG. 1 and FIG. 2) and one or more biometric signals. FIG. 7 shows an exemplary ECG sensing wearable device 600 that may included a chest mount 610, wrist mount 620, or both. Chest mount housing 610 may include a plurality of sensors 612 and chest strap 614, while the wrist-based device may include a wrist strap 620 and sensor 622. It is also appreciated that housing 610 may also comprise adhesive-based foam/cloth/tape backing (without strap) commonly used in the art for ECG electrodes/leads.

It is appreciated that the system 600 of FIG. 7 is shown as in a preferred embodiment as an ECG monitoring device. However, the systems and methods of the present invention may be used on a number of devices for measuring different types of biometric signals where location of the sensors has an impact on the environmental/biological data being acquired. For example, system 600 may be configured for use in acquiring pulse rate, heart rate, or respiration rate, or EMG, spatial range of limb motion, blood oxygenation from a pulse oximeter, temperature, etc.

As seen in FIG. 7, the chest mount 610 may have an installed location variation both vertically and horizontally along the torso 610 of the user, while the wrist device 620 may have varying location along the length of the arm, as well as rotationally around the arm.

Figure 8:
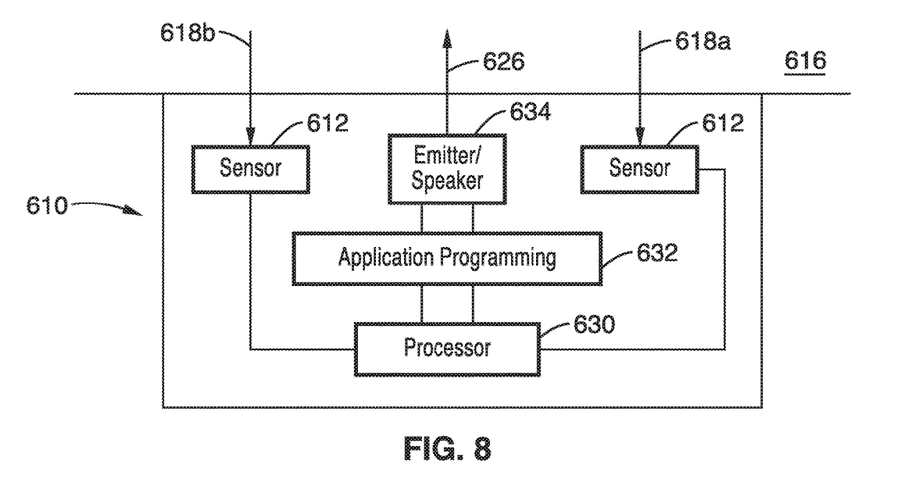
FIG. 8 schematic component diagram of an embodiment of a smart wearable device having bio-signal feedback

FIG. 8 shows a schematic diagram of the components of the chest-mounted wearable device 610. It is appreciated that wearable device 600 may also include additional circuitry as shown in the wearable device 104-1 in FIG. 2. Housing 610 is configured to disposed adjacent the skin to receive biometric signals from the user's torso 616. Sensors 612 may receive biometric signals 618a and 618b of varying strength depending on the location of the sensors 612. Upon receiving the biometric signals 618a, 618b, the application programming 632 (which may comprise code 206 in FIG. 2, or a module thereof) analyzes the incoming data from the biometric signals and provides a feedback signal 626 via an emitter/speaker 634.

In one embodiment, feedback signal 626 may comprise an audible sound (e.g. from a speaker 634) indicating placement on the human body, with the amplitude of the sound increasing as the signal strength (measured as SNR of the signal when compared to a template of known ECG waveforms) increases. After this initial placement phase, (which may last a couple of minutes), the feedback sound signal 326 may be disabled automatically or by the user. The user or device may at any time in the future re-enable the feedback signal 326 to provide the person with feedback if SNR decreases below a certain threshold, indicating that the wearable device needs to be repositioned.

It is appreciated that signal strength is one of many feedback signals that may be used to provide placement information to the user. In one alternative embodiment, the feedback data relayed to the user may be a function of impedance between two electrodes (e.g. between left and right instances of electrodes 612, 622 or a combination on thereof). Such impedance data may provide an indication of quality of contact with the wearer's skin 616. This impedance feedback may be provided in addition to, or independent of, the SNR of signal of interest (e.g. ECG in the above example), or other signal characteristics.

Figure 9:
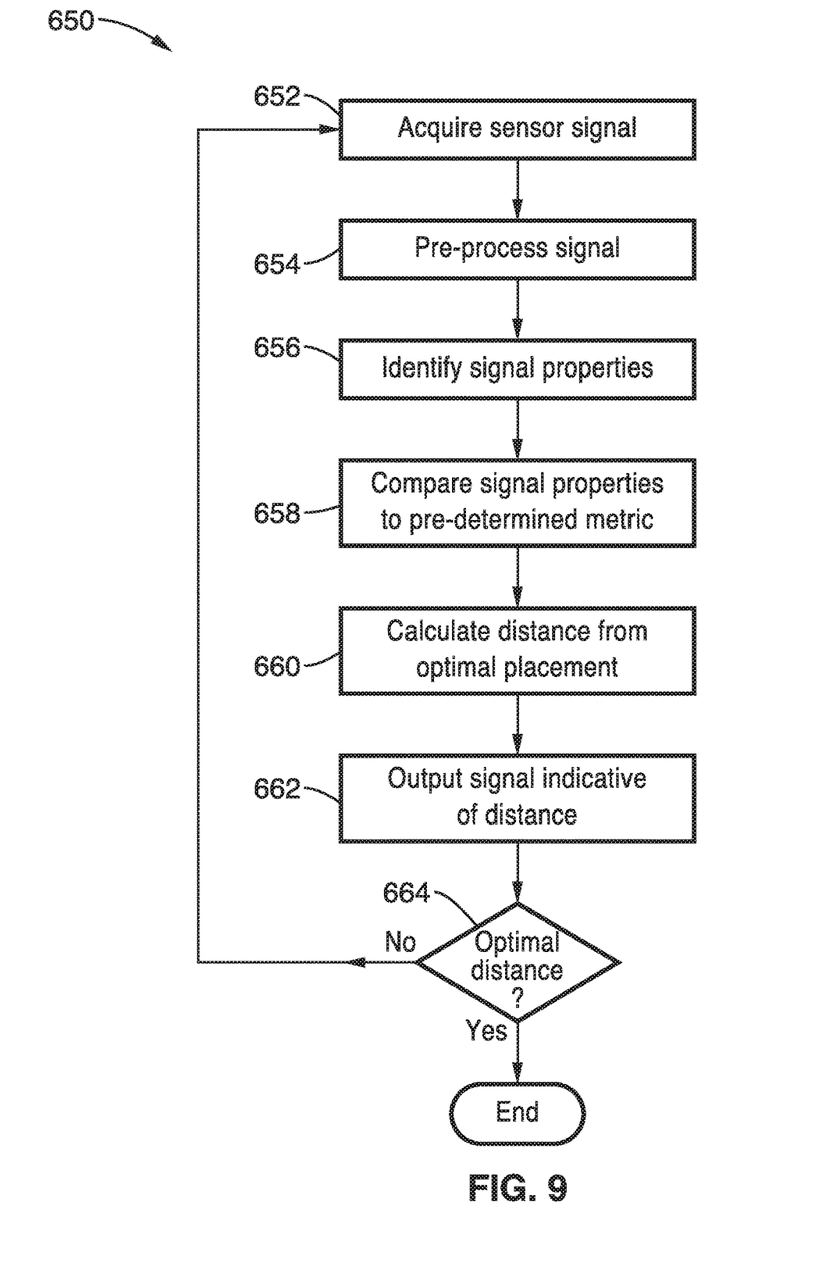
FIG. 9 shows a flow diagram of a method for providing bio-signal feedback for a wearable device as described herein.

FIG. 9 illustrates a method 650 for providing bio-signal feedback for a wearable device in accordance with the present description. Method 650 may be implemented as application programming 632 (FIG. 8) and/or code 206 (FIG. 2). At step 652, the sensor signals (e.g. bio-signals 618a and 618b) are acquired by the sensors. Next, pre-processing is performed at step 656 (e.g. filtering, amplification, and then processed in analog domain or digitized and processed in digital domain, and in spatial and/frequency domain). The signal properties are then identified at step 656. Pattern recognition may be applied to identify the signal of interest (in either digital or analog domain). At step 658, the identified signal properties may then be compared to a predetermined metric which may optionally be used to determine how far the sensors are away from an optimal placement (e.g. distance measurement step 660). At step 662, the output signal 626 may be emitted at a volume, intensity, frequency, tone, etc. to provide an audible indication of the sensor's proximity to ideal placement. If the location of the wearable device 610 is not optimal at step 664, the wearable device can continue acquiring signals (back at step 652) until optimal or acceptable placement is achieved. During this time, the user may adjust the location of the wearable device 610, and receive increasing/decreasing intensity signals to indicate whether they are getting "hotter" or "colder" to the ideal placement.

It is appreciated that variations on the "SNR" procedure may be alternatively employed. It should be noted that the "signal to noise" ratio is used here only as a loose term, as an indication of the quality of the measured signal of interest. Therefore "SNR" can depend on the type of processing performed on the signal by the device. This is particularly true for non-stationary or quasi-periodic signals. However, in all cases it is possible to estimate a metric that indicates the "strength" or "quality" of the signal being measured in context of signal of interest for the measurement.

In another embodiment, during initial placement on the body, the user may perform certain tasks to estimate SNR during performance of normal tasks in life, or performance of specific tasks of relevance to use of the device, and not just initial placement when the wearer is stationary or in another relaxed position.

Output signal 626 may also be configured to vary inversely (e.g. with decreasing intensity as the wearable device 610 is positioned further from the optimal location. Output signal 626 may also vary in differing means with SNR such that other types of feedback may be provided instead of or in addition to sound. For example, signal 626 may comprise light emission via LEDs as emitter 634 (in cases where the wearable device is visible to the person).

Emitter 634 may also be configured to emit vibration and other tactile methods (for more personal or discrete indications), sound transmission via bone conduction (for privacy), slight electrical stimulation on the person's or wearer's body, or wireless transmission to a remote device where the person (who may be the wearer or monitor or other person such as care giver) is notified using light, sound, tactile feedback, etc., or simply recorded for future reference.

In another embodiment, feedback may be presented to the user based on not only the signal characteristics as discussed above but also based on the anatomical location of the sensor on the user's body, for example by detecting the supraorbital ridge using optical or other sensing. The location of the sensor on the body may be estimated by the sensor itself, or by another sensor on the same device.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors, such as, for example, location, a timing event, detection of an object, detection of a facial expression, detection of location, detection of a change in location, or other factors. It will further be appreciated that as used herein, that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A wearable device, comprising: (a) a housing, wherein the housing supports one or more components of a wearable device; (b) one or more environmental sensors, wherein at least one sensor is configured for sensing a biometric signal corresponding to biological or physiological characteristics of a user; (c) a processor; and (d) programming stored in a non-transitory medium, wherein the programming is readable and executable by the processor, and wherein the programming performs steps comprising: (i) acquiring a biometric signal from the one or more environmental sensors; (ii) acquiring position data corresponding to a location of the one or more environmental sensors or housing with respect to the biometric signal; and (iii) adjusting operation of the wearable device as a function of the acquired position data.

2. A wearable device as in any of the previous embodiments, wherein the position data is acquired from the one or more environmental sensors.

3. A wearable device as in any of the previous embodiments, wherein the position data is acquired from a dedicated sensor separate from the one or more environmental sensors.

4. A wearable device as in any of the previous embodiments: wherein the programming is further configured for coupling the wearable device to a remote server; and receiving one or more device settings from the remote server; wherein the one or more device settings adjust the operation of the wearable device.

5. A wearable device as in any of the previous embodiments, wherein the one or more device settings are a function of the acquired position data.

6. A wearable device as in any of the previous embodiments, the one or more device settings modify acquisition of the biometric signal from the one or more environmental sensors.

7. A wearable device as in any of the previous embodiments, wherein the one or more device settings are stored in memory in the wearable device.

8. A wearable device, comprising: (a) one or more environmental sensors, wherein at least one sensor is configured for sensing a biometric signal corresponding to biological or physiological characteristics of a user; (b) a processor; and (c) programming stored in a non-transitory medium, wherein the programming is readable and executable by the processor, and wherein the programming performs steps comprising: (i) acquiring a biometric signal from the one or more environmental sensors; (ii) acquiring position data corresponding to a location of the one or more environmental sensors with respect to the biometric signal; and (iii) adjusting operation of the wearable device as a function of the acquired position data.

9. A wearable device as in any of the previous embodiments, wherein the position data is acquired from the one or more environmental sensors.

10. A wearable device as in any of the previous embodiments, wherein the position data is acquired from a dedicated sensor separate from the one or more environmental sensors.

11. A wearable device as in any of the previous embodiments: wherein the programming is further configured for coupling the wearable device to a remote server; and receiving one or more device settings from the remote server; wherein the one or more device settings adjust the operation of the wearable device.

12. A wearable device as in any of the previous embodiments, wherein the one or more device settings are a function of the acquired position data.

13. A wearable device as in any of the previous embodiments the one or more device settings modify acquisition of the biometric signal from the one or more environmental sensors.

14. A wearable device as in any of the previous embodiments, wherein the one or more device settings are stored in memory in the wearable device.

15. A method for providing biometric signal feedback for a wearable device comprising: acquiring a biometric signal from the one or more environmental sensors, the biometric signal corresponding to biological or physiological characteristics of a user; acquiring position data corresponding to a location of the one or more environmental sensors with respect to the biometric signal; and adjusting operation of the wearable device as a function of the acquired position data.

16. A method as in any of the previous embodiments, wherein the position data is acquired from the one or more environmental sensors.

17. A method as in any of the previous embodiments, wherein the position data is acquired from a dedicated sensor separate from the one or more environmental sensors.

18. A method as in any of the previous embodiments, further comprising: coupling the wearable device to a remote server; receiving one or more device settings from the remote server; and adjust the operation of the wearable device based on the acquired one or more device settings.

19. A method as in any of the previous embodiments wherein the one or more device settings are a function of the acquired position data.

20. A method as in any of the previous embodiments, the one or more device settings modify acquisition of the biometric signal from the one or more environmental sensors.

21. A wearable device, the device comprising: (a) a housing, wherein the housing supports one or more components of a wearable device; (b) one or more sensors, wherein at least one sensor is configured for sensing a biometric signal corresponding to biological or physiological characteristics of a user; (c) an emission source; (d) a processor; and (e) programming stored in a non-transitory medium or downloaded to the processor from an external non-transitory medium or storage, wherein the programming is readable and executable by the processor, and wherein the programming performs steps comprising: (i) acquiring a biometric signal from the one or more sensors; (ii) identifying one or more properties of the signal, the one or more signal properties corresponding to a location of the one or more sensors with respect to the biometric signal; and (iii) outputting a feedback signal via the emission source, the feedback signal indicating a proximity of the one or more sensors with respect to the biometric signal as a function of the one or more signal properties of the biometric signal.

22. A wearable device as in any of the previous embodiments, wherein the one or more signal properties comprises the strength of the signal.

23. A wearable device as in any of the previous embodiments, wherein the one or more signal properties comprises the signal to noise ratio (SNR) of the signal.

24. A wearable device as in any of the previous embodiments, wherein the programming is further configured for comparing the one or more identified properties to a predetermined metric; and varying the output of the feedback signal based on said comparison.

25. A wearable device as in any of the previous embodiments, wherein the output feedback signal is varied by one or more of intensity, magnitude, frequency, or tone to indicate proximity of the one or more sensors with respect to an optimal location on the user.

26. A wearable device as in any of the previous embodiments, wherein the output feedback signal comprises an emission of one or more of: light, sound, vibration, electrical stimulation, or wireless transmission.

27. A wearable device as in any of the previous embodiments, wherein the biometric signal comprises and ECG waveform.

28. A wearable device, the device comprising: (a) one or more sensors, wherein at least one sensor is configured for sensing a biometric signal corresponding to biological or physiological characteristics of a user; (b) a processor; and (c) programming stored in a non-transitory medium, wherein the programming is readable and executable by the processor, and wherein the programming performs steps comprising: (i) acquiring a biometric signal from the one or more sensors; (ii) identifying one or more properties of the signal, the one or more signal properties corresponding to a location of the one or more sensors with respect to the biometric signal; and (iii) outputting a feedback signal a proximity of the one or more sensors with respect to the biometric signal as a function of the one or more signal properties of the biometric signal.

29. A wearable device as in any of the previous embodiments, wherein the one or more signal properties comprises the strength of the signal.

30. A wearable device as in any of the previous embodiments, wherein the one or more signal properties comprises the signal to noise ratio (SNR) of the signal.

31. A wearable device as in any of the previous embodiments, wherein the programming is further configured for comparing the one or more identified properties to a predetermined metric; and varying the output of the feedback signal based on said comparison.

32. A wearable device as in any of the previous embodiments, wherein the output feedback signal is varied by one or more of intensity, magnitude, frequency, or tone to indicate proximity of the one or more sensors with respect to an optimal location on the user.

33. A wearable device as in any of the previous embodiments, wherein the output feedback signal comprises an emission of one or more of: light, sound, vibration, electrical stimulation, or wireless transmission.

34. A wearable device as in any of the previous embodiments, wherein the biometric signal comprises and ECG waveform.

35. A method for providing biometric signal feedback for a wearable device comprising: (i) acquiring a biometric signal from one or more sensors; (ii) identifying one or more properties of the biometric signal, the one or more signal properties corresponding to a location of the one or more sensors with respect to the biometric signal; and (iii) outputting a feedback signal a proximity of the one or more sensors with respect to the biometric signal as a function of the one or more signal properties of the biometric signal.

36. A method as in any of the previous embodiments, wherein the one or more signal properties comprises the strength of the signal.

37. A method as in any of the previous embodiments, wherein the biometric signal comprises and ECG waveform; and wherein the one or more signal properties comprise the signal to noise ratio (SNR) of the ECG waveform.

38. A method as in any of the previous embodiments, further comprising: comparing the one or more identified properties to a predetermined metric; and varying the output of the feedback signal based on said comparison.

39. A method as in any of the previous embodiments, wherein the output feedback signal is varied by one or more of intensity, magnitude, frequency, or tone to indicate proximity of the one or more sensors with respect to an optimal location on the user.

40. A method as in any of the previous embodiments, wherein the output feedback signal comprises an emission of one or more of: light, sound, vibration, electrical stimulation, or wireless transmission.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for" or "step for".

What is claimed is:

1. A wearable device, comprising:
    (a) a housing in the form of eyewear configured to be disposed on a facial surface of a user, wherein the housing supports one or more components of the wearable device;
    (b) one or more environmental sensors, wherein at least one sensor is configured for sensing a biometric signal corresponding to biological or physiological characteristics of a user;
    (c) a processor; and
    (d) programming stored in a non-transitory medium, wherein the programming is readable and executable by the processor, and wherein the programming performs steps comprising:
        (i) acquiring a biometric signal from the one or more environmental sensors;
        (ii) acquiring position data corresponding to a location of the one or more environmental sensors or housing with respect to the biometric signal and the facial surface; and
        (iii) adjusting operation of the wearable device as a function of the acquired position data.

2. The wearable device of claim 1, wherein the position data is acquired from the one or more environmental sensors.

3. The wearable device of claim 1, wherein the position data is acquired from a dedicated sensor separate from the one or more environmental sensors.

4. The wearable device of claim 1:
    wherein the programming is further configured for coupling the wearable device to a remote server; and
    receiving one or more device settings from the remote server;
    wherein the one or more device settings adjust the operation of the wearable device.

5. The wearable device of claim 4, wherein the one or more device settings are a function of the acquired position data.

6. The wearable device of claim 5, the one or more device settings modify acquisition of the biometric signal from the one or more environmental sensors.

7. The wearable device of claim 4, wherein the one or more device settings are stored in memory in the wearable device.

8. A method for providing biometric signal feedback for a wearable device comprising:
    positioning eyewear on a facial surface of a user, the eyewear comprising one or more environmental sensors;
    acquiring a biometric signal from the one or more environmental sensors, the biometric signal corresponding to biological or physiological characteristics of a user;
    acquiring position data corresponding to a location of the one or more environmental sensors with respect to the biometric signal and the facial surface; and
    adjusting operation of the wearable device as a function of the acquired position data.

9. The method of claim 8, wherein the position data is acquired from the one or more environmental sensors.

10. The method of claim 8, wherein the position data is acquired from a dedicated sensor separate from the one or more environmental sensors.

11. The method of claim 8, further comprising:
    coupling the wearable device to a remote server;
    receiving one or more device settings from the remote server; and
    adjust the operation of the wearable device based on the acquired one or more device settings.

12. The method of claim 11, wherein the one or more device settings are a function of the acquired position data.

13. The method of claim 12, the one or more device settings modify acquisition of the biometric signal from the one or more environmental sensors.

14. A wearable device, the device comprising:
    (a) a housing, wherein the housing supports one or more components of the wearable device;
    (b) one or more sensors, wherein at least one sensor is configured for sensing a biometric signal corresponding to biological or physiological characteristics of a user;
    (c) an emission source;
    (d) a processor; and
    (e) programming stored in a non-transitory medium, wherein the programming is readable and executable by the processor, and wherein the programming performs steps comprising:
        (i) acquiring a biometric signal from the one or more sensors;
        (ii) identifying one or more properties of the signal, the one or more signal properties corresponding to a location of the one or more sensors with respect to the biometric signal; and
        (iii) outputting a feedback signal via the emission source, the feedback signal indicating a proximity of the one or more sensors with respect to the biometric signal as a function of the one or more signal properties of the biometric signal.

15. The wearable device of claim 14, wherein the one or more signal properties comprises the strength of the signal.

16. The wearable device of claim 14, wherein the one or more signal properties comprises the signal to noise ratio (SNR) of the signal.

17. The wearable device of claim 14, wherein the programming is further configured for comparing the one or more identified properties to a predetermined metric; and
    varying the output of the feedback signal based on said comparison.

18. The wearable device of claim 14, wherein the output feedback signal is varied by one or more of intensity, magnitude, frequency, or tone to indicate proximity of the one or more sensors with respect to an optimal location on the user.

19. The wearable device of claim 14, wherein the output feedback signal comprises an emission of one or more of: light, sound, vibration, electrical stimulation, or wireless transmission.

20. The wearable device of claim 14, wherein the biometric signal comprises and ECG waveform.

* * * * *